United States Patent [19]

Eikenberry et al.

[11] 4,132,528
[45] Jan. 2, 1979

[54] ANALYTICAL ELEMENT FOR THE ANALYSIS OF LIQUIDS UNDER HIGH PH CONDITIONS

[75] Inventors: Jon N. Eikenberry; Karl J. Sanford; Richard C. Sutton, all of Rochester, N.Y.

[73] Assignee: Eastman Kodak Company, Rochester, N.Y.

[21] Appl. No.: 866,731

[22] Filed: Jan. 3, 1978

[51] Int. Cl.² .................... G01N 31/22; G01N 33/16
[52] U.S. Cl. .................................. 23/230 B; 252/408; 422/57
[58] Field of Search ............... 23/253 TP, 230 B; 252/408

[56] References Cited

U.S. PATENT DOCUMENTS

| | | | |
|---|---|---|---|
| 3,310,382 | 3/1967 | Kingsley | 23/230 B |
| 3,379,528 | 4/1968 | Henn et al. | 96/28 |
| 3,485,587 | 12/1969 | Keston | 252/408 X |
| 3,807,956 | 4/1974 | Morin | 23/230 B |
| 3,992,158 | 11/1976 | Przybylowicz et al. | 23/253 TP |

FOREIGN PATENT DOCUMENTS 2513840  4/1974  Fed. Rep. of Germany.

OTHER PUBLICATIONS

Gornall et al., J. Biol. Chem. 177, 751 (1949).

*Primary Examiner*—Robert M. Reese
*Attorney, Agent, or Firm*—Ronald P. Hilst

[57] ABSTRACT

An improved analytical element for the detection of a predetermined analyte in an aqueous liquid under highly alkaline conditions is disclosed. The element features a stable, alkaline-providing composition.

Preferably, the analytical element is a multi-zone element. The element is particularly useful in total protein analysis and, when so used, an improved biuret reagent composition for use therein is also provided. Methods of using the aforementioned analytical and biuret reagent composition are also disclosed.

46 Claims, 1 Drawing Figure

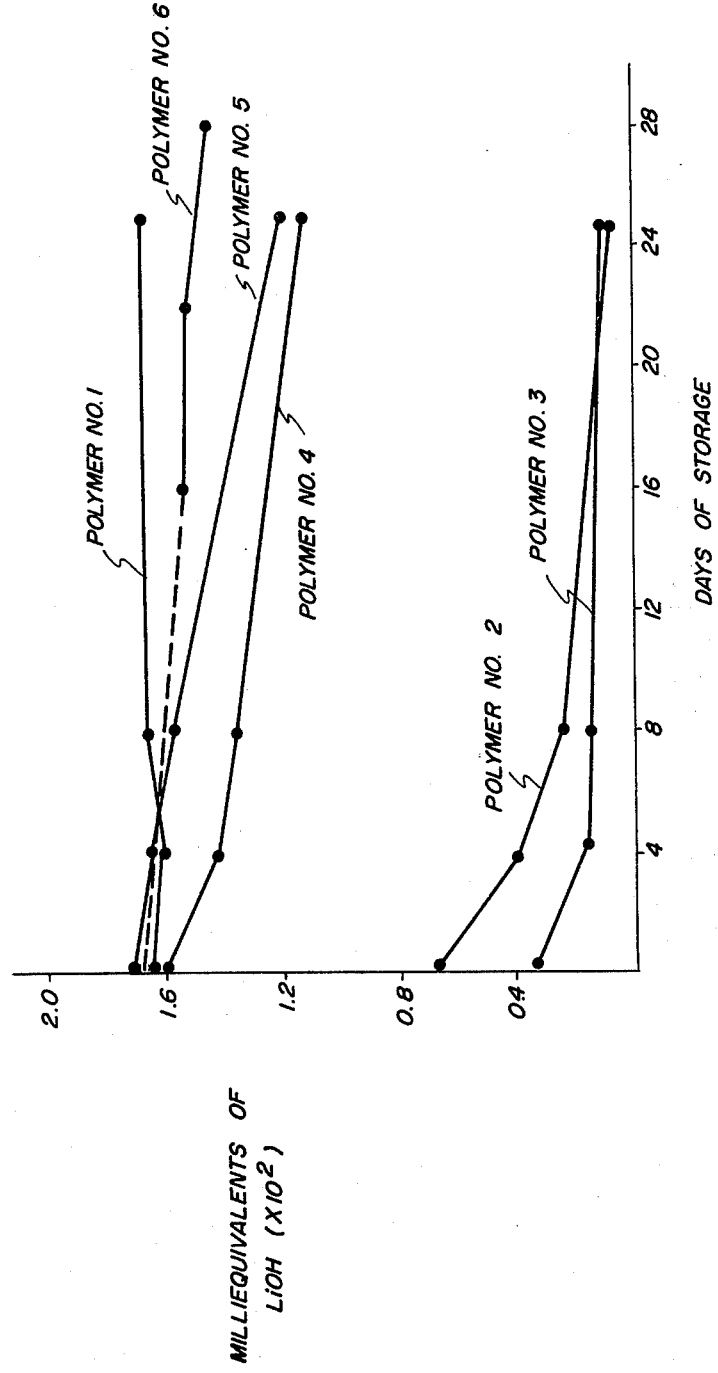

ANALYTICAL ELEMENT FOR THE ANALYSIS OF LIQUIDS UNDER HIGH PH CONDITIONS

FIELD OF THE INVENTION

The present invention relates to an element useful for the chemical analysis of aqueous liquids under high pH conditions. In one embodiment, there is specifically disclosed an element for the chemical analysis of protein materials contained in an aqueous liquid.

DESCRIPTION OF RELATED ART

It is often desirable or necessary to determine the presence and/or concentration of certain substances in aqueous liquids, particularly biological liquids such as blood, serum and urine. In the past, a variety of so-called "wet chemistry" devices and methods have been employed for such analyses. In such "wet chemistries" clinical reagents are dissolved or suspended in a liquid aqueous vehicle. Although useful, wet chemistry assay techniques, sometimes referred to as solution assays, typically require analyzer equipment having intricate solution handling and transport capabilities. Analytical equipment of this "wet chemistry" variety, illustrated for example in U.S. Pat. No. 2,797,149, is often expensive and complex in terms of liquid handling requirements.

As an alternative to the aforementioned "wet chemistry" assay techniques and because of convenience, low cost, and the rapidity by which analyses can be carried out, it has often been found desirable to carry out analysis of aqueous liquids by use of various so-called "dry-chemistry" techniques. As used herein, "dry-chemistry" assays or techniques have reference, for example, to analytical chemical techniques which are performed using reagent compositions, sometimes referred to hereinafter as interactive compositions, incorporated in various substantially "dry-to-the-touch" elements. Typical "dry-to-the-touch" analytical elements include "dip and read" test strips and multi-zone analytical test elements, e.g., multilayer analytical elements. A group of "dry chemistry" multilayer analytical elements which has recently been developed and found to be particularly effective in producing quantitative analytical results is described in Przybylowicz and Millikan, U.S. Pat. No. 3,992,158, issued Nov. 16, 1976; Clement, U.S. Pat. No. 4,042,335 issued Aug. 16, 1977; Wu et. al. U.S. Pat. application Ser. No. 759,529 filed Jan. 14, 1977, now U.S. Pat. No. 4,069,017; and Figueras, U.S. patent application Ser. No. 759,527, filed Jan. 14, 1977 now abandoned.

In the past, depending upon the particular substance under analysis, sometimes referred to hereinafter as analyte, or upon the particular interactive composition(s) contained in the test element for determining the presence of the desired analyte, it has often been necessary to conduct a particular analysis under high pH conditions, for example, a pH in excess of about 12.0. For instance, it has been found useful to analyze aqueous liquids such as serum and urine for their protein content by use of a biuret reagent composition. A biuret reagent composition, as is well known, has reference to the use of an interactive composition containing the cupric form of copper in the presence of a base of sufficient strength to provide a pH in excess of about 12.0. When protein in an aqueous fluid such as serum interacts with the biuret reagent, a reaction between the cupric form of copper and the protein occurs at this high pH to produce a violet color. Typically, the determination of the protein content of an aqueous fluid, such as human serum, by use of a biuret reagent is carried out as a solution assay or "wet chemistry" technique.

A general review of the biuret reaction as a solution assay technique may be found, for example, in the article entitled "Determination of Serum Proteins by Means of the Biuret Reaction" prepared by A. G. Gornall, C. J. Bardawill, and M. M. David appearing in J. Biol. Chem., Volume 177, page 751 (1949). As will be appreciated, various modifications and variations of the biuret technqiue for the determination of protein in biological fluids have been developed since the publication of the foregoing article. One such modified technique is described in German Patent Application No. 2,513,840 published Oct. 23, 1975. In this wet chemistry technique, protein determination in solution takes place by (a) heating a sample of the protein-containing solution with a specified biuret reagent material until a color is developed, (b) separating undissolved material from the liquid sample to be analyzed, and then (c) determining the protein content of the sample colorimetrically. As will be apparent, this technique, although a modified version of the original biuret assay, remains a wet chemistry technique.

As an attempt to simplify the above-described biuret technique for the assay of protein contained in various biological fluids, there have been developed in the art various so-called "dry" biuret reagent compositions as described in U.S. Pat. No. 3,310,382, issued Mar. 21, 1967. In essence, these "dry" compositions are dry powders composed of a physical mixture of the biuret reagent components including, a basic compound, a copper salt and, if desired, copper chelating agents (such as sodium potassium tartrate, citrates, and the like), and various surfactants. Although the aforementioned powder is "dry," the actual assay using this powder remains essentially a wet chemistry assay. That is, at the time of the assay, the "dry" biuret reagent powder is physically dissolved in a container of distilled water, for example, a test tube, the aqueous protein-containing sample is then added thereto, and the resultant color of the solution which develops is measured spectrophotometrically. Accordingly, although this modification of the original biuret assay technique uses a dry powder biuret reagent composition, the assay which employs this reagent is carried out as a conventional wet chemistry technique.

Yet another modification of the biuret reaction for the analysis of protein in biological fluids is described in U.S. Pat. No. 3,807,956 issued Apr. 30, 1974. In this modification of the biuret technique, rather than premix the biuret reagent composition as a dry powder as described in the above-noted U.S. Pat. No. 3,310,382, the biuret reagent composition is premixed in an aqueous zirconium-containing solution and the solution may then be stored, for example, in a sealed ampule, until needed. At the time the assay using such a biuret reagent solution is to be performed, the ampule is broken and the contents added to a protein-containing aqueous test sample. The resultant level of color which forms can then be measured spectrophotometrically.

As can be seen from the foregoing review of the art, the biuret technique for the assay of protein in biological fluids remains essentially a "wet chemistry" assay technique, although certain modifications have been developed in an effort to improve or simplify the technique. As will be appreciated, it would be highly advantageous to convert this useful wet chemistry assay technique to one which can readily be performed as a "dry chemistry" analytical technique using, for example, a "dip and read" test strip where qualitative or semiquantitative results are desired, or a multi-zone analytical element, such as a multilayer analytical element, where more precise, quantitative results are desired. However, when an attempt is made to prepare and use typical dry chemistry analytical elements containing a biuret reagent composition, or any other interactive composition which requires a highly alkaline environment, serious problems are encountered.

All aspects of these problems are not yet fully understood. However, it appears that when one attempts to incorporate highly basic compounds into dry chemistry analytical elements, one encounters the problem that many compounds capable of providing highly alkaline conditions, for example, sodium hydroxide, undergo rapid deterioration of their initially high pH generating capacity. Accordingly, within a fairly rapid period of time, e.g., 8 to 10 days, a typical dry chemistry analytical element which contains the above-noted basic compounds, although initially capable of providing high pH conditions (when contacted with an aqueous sample containing the desired analyte), is no longer capable of providing a high pH environment. And, therefore, the desired reaction between the analyte and the reagent composition which requires a highly alkaline environment either can no longer take place or is substantially inhibited.

SUMMARY OF THE INVENTION

In accord with the present invention there is provided an improved analytical element and method for the detection of a predetermined analyte in an aqueous liquid under highly alkaline conditions, i.e., pH conditions in excess of about 12.0. An element of the present invention includes a zone to distribute the aqueous liquid under analysis and, associated with this zone, a reagent composition that provides a detectable change within the element upon interaction of the element with analyte-containing liquid. The specific features which characterize an improved element in accord with the present invention comprise the incorporation in the element of a stable, alkaline-providing composition substantially free from sodium ion and comprising, in admixture, an amount of base sufficient to provide a pH in excess of about 12.0 in the element under conditions of use thereof and an alkaline protective polymer.

The stable, alkaline-providing compositions featured in the analytical elements of the present invention are broadly applicable to a wide variety of analytical elements including the above-referenced "dip and read" test strips and the above-referenced multi-zone analytical elements such as integral multilayer elements of the type described in the above-referenced U.S. Pat. Nos. 3,992,158; 4,042,335; and U.S. Ser. Nos. 759,527 and 759,529.

In addition, the present invention has similar broad applicability with respect to the various reagent composition(s) that can be employed in an analytical element in conjunction with the stable, alkaline-providing compositions described herein.

In accord with an especially preferred embodiment of the invention, the stable, alkaline-providing composition described herein is incorporated in an analytical element containing as a reagent composition a biuret composition. In a highly alkaline environment a biuret reagent composition interacts with and provides for the detection of protein in an aqueous liquid.

In accord with a further aspect of the invention, an improved biuret reagent composition and a method using the same are provided. The biuret reagent composition of the invention is substantially free from sodium ion and comprises a water soluble cupric salt, such as copper sulfate, a chelating agent precursor for the cupric salt, and an amount of base sufficient to provide a pH in excess of about 12.0 under conditions of use of the biuret composition. An especially useful chelating agent precursor for the aforementioned biuret reagent composition is tartaric acid. In a highly alkaline environment tartaric acid is converted to the tartrate form thereof, thus providing a chelating agent for the cupric salt.

The biuret reagent compositions of the invention are particularly useful in the above-described "dry chemistry" analytical elements and methods. However, these reagent compositions have general utility for the detection of protein in an aqueous liquid sample and therefore can advantageously be employed in both "wet chemistry" and "dry chemistry" analyses of aqueous liquids.

BRIEF DESCRIPTION OF THE DRAWING

The accompanying drawing

FIG. 1 is a graph illustrating the suitability of certain polymers as alkaline protective polymers useful in the present invention.

DETAILED DESCRIPTION OF THE PREFERRED EMBODIMENTS

In accord with certain preferred embodiments, the present invention is advantageously embodied in a multi-zone analytical element of the type described in U.S. Ser. No. 759,529, especially multilayer analytical elements such as described in the aforementioned U.S. patent application as well as in U.S. Pat. Nos. 3,992,158; 4,042,335; and U.S. Ser. No. 759,527. In such multi-zone analytical elements there is typically present a spreading zone to transport the aqueous liquid sample under analysis and to distribute or meter the liquid sample within the analytical element. This spreading zone can therefore serve as the zone to distribute the aqueous liquid under analysis in accord with the present invention.

In these multi-zone elements there is also typically present an associated reagent zone which includes a reagent composition. The multi-zone elements are structured such that the reagent zone is associated with the spreading zone, thereby permitting the spreading zone to distribute the liquid test sample into fluid contact with the reagent zone.

The suitable, alkaline-providing composition described hereinabove, which constitutes an essential feature of the present invention, may be incorporated in a multi-zone element in either the above-described spreading zone or reagent zone. Alternatively, it may be present in such a multi-zone element in a separate zone of the element which, in turn, is in fluid contact with the spreading zone and reagent zone of the element under conditions of use. Thus, an applied aqueous sample is capable of coming into fluid contact and interacting with this alkaline-providing composition to provide the desired alkaline environment within one or more zones of the element.

In accord with a further embodiment of the multi-zone elements of the present invention, these elements are structured as integral elements wherein the spreading zone, reagent zone, and any other zones are defined in the element by superposed layers carried on a suitable support, such as a "radiation-transmissive" support.

As used herein, the term "radiation-transmissive" describes zones, supports and other layers of an analytical element that permit effective passage of electromagnetic radiation used to detect an analytical result produced in the element. Accordingly, in those analytical elements of the invention wherein the analytical result produced is detectable by virtue of a visible color change produced in the element, such transmissiveness would include transmission of electromagnetic radiation of a wavelength or wavelengths within the visible region between about 400 nanometers and 700 nanometers. Alternatively, where the analytical result produced is detected by electromagnetic radiation outside the visible wavelength range, a "radiation transmissive" zone, layer, or support for such an element would be transmissive of this specific radiation, whatever it might be including, for example, ultraviolet radiation, infrared radiation, or that produced by radioactivity.

As explained hereinabove, the various individual zones of a multi-zone analytical element of the invention are, at least under conditions of use, in fluid contact with one another. The term "fluid contact" as used herein has reference to the ability of an aqueous liquid to pass between superposed or abutting zones of an analytical element. Although zones in fluid contact can be contiguous, they may also be separated by intervening zones, providing, however, that such physically intervening zones will also be in such fluid contact and will not prevent the passage of fluid therebetween.

Fluid contact between zones of the preferred multi-zone elements of the present invention can be achieved by preparing such elements having zones that are initially contiguous or effectively so for purposes of fluid passage. Alternatively, it may be appropriate to prepare elements that have zones initially non-contiguous, and which further can be spaced apart, such as by the use of interleaves or by the use of a resilient absorbent material or a deformable support. As will be appreciated, if the element has initially non-contiguous zones, it may be necessary to apply compressive force or otherwise provide means to bring such non-contiguous zones of the element into fluid contact at the time of its use to provide useful analytical results.

The above-described preferred multi-zone analytical elements, particularly the integral multilayer analytical elements noted above, have been found especially effective in accord with the present invention because these elements have been found capable of providing highly quantitative analytical results without the use of specialized procedures such as sample confinement, removal of excess sample, and the like that require the use of skilled, specially trained clinical personnel. Further, these elements readily lend themselves to the use of automated means of measuring analytical results so that the analytical measurements to be detected from these elements can be done quickly and with minimal risk of error.

In accord with yet another aspect of the present invention, it will be appreciated that the invention can also be readily embodied in less quantitative analytical elements, such as "dip and read" test strips. Although these test strips generally do not require as much precision or accuracy in their manufacture and are less complex in their physical structure, these elements can also be highly useful, for example, in situations where one desires to obtain qualitative or semiquantitative results.

Such test strips may be composed, in their simplest form, of a single layer which serves as the zone which distributes the aqueous liquid under analysis. Typically, this single layer is composed of a fibrous material, such as a synthetic or natural fibrous material, e.g., a nylon mesh or a filter paper material, in which there is impregnated or imbibed one or more active materials serving as a reagent composition for the element. In accord with the present invention, the stable, alkaline-providing compositions described herein can also be incorporated in this single layer of the test strip or in an associated layer or zone of the test strip which is in fluid contact with the reagent composition under conditions of use of the test strip. In operation, the resultant test strip is treated with an aqueous liquid containing the analyte of choice, such as by dipping the test strip into the liquid or contacting the strip with the liquid, thereby permitting the liquid to permeate into the strip. As a result, the analyte of choice interacts with the strip under the highly alkaline conditions which are created as the aqueous liquid activates the alkaline-providing composition incorporated therein, and a detectable change is produced in the strip.

As indicated hereinabove, an essential feature of the analytical elements provided by the present invention is a stable, alkaline-providing composition. This composition comprises two necessary ingredients, namely an amount of base sufficient to provide a pH in excess of about 12.0 within the analytical element under conditions of use thereof and an alkaline protective polymer.

Although the precise reasons are not fully understood, the stability of these alkaline-providing compositions, i.e., the capability of these compositions to provide highly alkaline conditions within the element in which they are incorporated even after the element has been exposed to ambient temperature and relative humidity conditions for an extended period, appears to depend, in large part, on maintaining these alkaline-providing compositions substantially free from sodium ion and by the incorporation in these compositions of the above-mentioned alkaline protective polymer. In particular, it is believed that although sodium ions can be used in many inorganic compounds to provide effective basic compounds, e.g., sodium hydroxide, anhydrous sodium carbonate, sodium orthophosphate, and the like, such basic sodium-containing compounds tend to be quite hydroscopic, even when admixed with an alkaline protective polymer and incorporated in analytical elements as provided in the present invention. As a result, these basic sodium-containing compounds tend to extract water vapor from the ambient atmosphere which, in turn, can combine with carbon dioxide also present in the ambient atmosphere, thereby leading to the formation of hydrogen carbonate and other carbonates within the analytical elements. Because of the buffering capacity exhibited by such carbonates, the initially highly alkaline condition which basic sodium compounds e.g., sodium hydroxide, can provide in an analytical element rapidly deteriorates to a level substantially below a pH of 12.0. Accordingly, reagent compositions which require a highly alkaline environment, such as a biuret reagent which exhibits optimum activity under alkaline conditions in excess of a pH of 12.0, display a substantially reduced activity and/or are rendered completely inactive.

A second major factor contributing to the stability of the alkaline-providing compositions featured in the elements of the present invention is the use in these compositions of the above-referenced alkaline protective polymer. That is, in accord with the present invention, it has been found that the alkaline pH generating capacity of highly basic compounds, even those which are free of sodium ion, such as lithium hydroxide, calcium hydroxide, and the like, tends to be substantially reduced in a relatively short period of time, e.g., 8–10 days, when incorporated within an analytical element. However, it has been found in accord with the present invention that by combining sodium-free basic compounds with certain polymers, herein designated "alkaline protective" polymers, one is advantageously and surprisingly provided an effective means for preventing or at least substantially reducing the aforesaid deterioration of the alkaline pH generating capacity of these basic compounds.

In the course of the investigation and research leading to the present invention, an off-line test which is relatively simple and inexpensive has been developed to ascertain whether a particular polymer exhibits useful "alkaline protective" capability such as required in the present invention. This test is as follows:

(1) A plastic film support such as a poly(ethylene terephthalate) film having a width of at least 2.5 cm. and a length in excess of about 100 cm. is used as a support on which is uniformly hand-coated in a continuous layer of an alkaline-providing test composition composed of the basic compound lithium hydroxide, a surfactant, and the particular polymer to be tested for its alkaline protective capability. The particular surfactant used in this test is Triton ® X-200, a salt of an alkylaryl polyether sulfonate, purchased from Rohm & Haas Company. It is believed that other similar surfactants could be substituted for Triton ® X-200 in this test without significantly affecting the test results. The lithium hydroxide, surfactant, and the polymer to be tested are coated from distilled water and the amounts of the lithium hydroxide, surfactant and polymer under test contained in the coating dope are adjusted such that the theoretical amount of lithium hydroxide laid down as a wet coating on the plastic film support is equivalent to about 2.7 g/m$^2$ of LiOH.H$_2$O, the amount of polymer laid down is about 8.0 g/m$^2$, and the amount of surfactant laid down is 0.54 g/m$^2$. The wet coated layer is then air-dried. It will be appreciated that the specific coating and air drying conditions, e.g., temperature, relative humidity, etc., will vary depending on the physical properties of the polymer under test. For example, the coating temperature is typically selected as a temperature at which the polymer exhibits substantially uniform coating, e.g., uniform film-forming, properties.

(2) A test patch in the form of a 1.6 cm. square is cut from the above-described coated plastic support within 3 hours of the initial coating operation described in step 1 above to determine the amount of base contained therein. This determination is carried out as follows:

A phenolphthalein indicator solution is prepared by adding five milligrams of phenolphthalein to ten milliliters of distilled water. Dissolution of the indicator is achieved by adding one drop of concentrated NaOH (i.e., a solution composed of 50% by weight NaOH and 50% by weight water) and titrating the solution to pH 8.9 with 1 M HCl. The coated test patch is then placed, coating side up, in a 25 ml scintillation vial. To the vial, 3 ml of distilled water is added; a small magnetic stirring bar is placed in the vial and the solution stirred for five minutes. To the stirred solution, 40 μl of the above-described phenophthalein indicator solution is added and the resultant solution titrated with 0.01 N HCl to a clear endpoint. The volume of acid required to reach the endpoint is noted.

If none of the lithium hydroxide is lost during the coating and drying operations of step (1) above, e.g., by carbon dioxide adsorption during these operations, etc., it is calculated that the theoretical amount of lithium hydroxide present in the test patch, as expressed in terms of the above-described titration procedure using 0.01N HCl is $1.70 \times 10^{-2}$ mEq. of lithium hydroxide. The remaining coated plastic support is stored in the ambient atmosphere at a temperature of approximately 21° C. at a relative humidity of about 50% for a period of at least 8 days. During this 8 day storage period, on each of the fourth and eighth day thereof, respectively, an additional 1.6 cm. square test patch is cut from the above-described coated plastic support and tested in a manner identical to that used for the first test patch to determine the amount of base contained therein.

(3) The quantity of base present in each of the three test patches as measured in steps 1 and 2 is evaluated and compared. If the absolute quantity of base measured in each of the test patches is equal to or exceeds about $0.8 \times 10^{-2}$ mEq. of lithium hydroxide, the particular polymer under test exhibits the necessary alkaline protective capacity rendering it useful in the present invention.

Several examples illustrating the use of the above-described test for evaluating the alkaline protective capacity of polymers useful in the present invention are provided hereinafter in the appended working examples. The results of such testing are provided in the graph illustrated in FIG. 1.

With the aid of the foregoing test, it will be appreciated that selection of specific alkaline protective polymers for use in the present invention is a relatively straight-forward task. Thus, a given polymer can be routinely evaluated to determine whether it is or is not "alkaline protective" and therefore useful in the present invention. Accordingly, the term "alkaline protective" as used in the present specification and claims can be defined in terms of the foregoing test.

A partial listing of specific representative polymers which have been found effective for use in the present invention based on their alkaline protective capability as evaluated in terms of the foregoing test include poly(vinyl pyrrolidone), poly(acrylamide), agarose, and particularly copolymers prepared from copolymerized monomer blends of vinyl pyrrolidone and acrylamide. The latter copolymers have been found especially useful because they not only exhibit alkaline protective capability, but in addition these copolymers exhibit good film-forming properties and readily adhere (in the presence of large amounts of base) to conventional plastic film supports composed of, for example, poly(ethylene terephthalate) or poly(ethylene terephthalate) which has been surface treated as described hereinafter to improve its adhesion to overlayers. In addition, these copolymers can readily be coated and dried without employing high temperature coating conditions, i.e., temperatures in excess of about 50° C., and without exhibiting undue sensitivity to drying time. Preferred copolymers are copolymers prepared from monomer blends containing from about 20 to about 80 weight % vinyl pyrrolidone and from about 80 to about 20 weight % acrylamide. Especially preferred are copolymers of acrylamide and vinyl pyrrolidone prepared from a monomer blend composed of equal weight amounts of acrylamide and vinyl pyrrolidone monomers.

Basic compounds which have been found useful as the base incorporated in the alkaline-providing compositions employed in the present invention include strong basic compounds substantially free from sodium ion such as lithium hydroxide, calcium hydroxide, mixtures thereof, and the like. Particularly preferred is lithium hydroxide which may be readily coated from aqueous coating dopes and which, when admixed with an appropriate alkaline protective polymer, has been found to be remarkably stable and retentive of a high degree of alkalinity. Of course, other substantially sodium-free strongly basic compounds can also be used within the scope of the present invention.

As stated hereinabove, the amount of base employed should be sufficient to provide a pH in excess of about 12.0 within the element under normal conditions of use thereof. The actual amount of base employed within a given element of the present invention will vary depending upon, for example, the particular degree of alkalinity which is desired to be maintained within the element or a portion thereof under conditions of use and the amount of aqueous liquid which permeates into the element under conditions of use thereof. That is, if the particular reagent composition selected is one which interacts with the analyte of choice at only exceptionally high pH values on the order of about 13.5 to 14, larger amounts of the base will be required than in the case where the particular reagent composition selected is one which interacts with the analyte of choice at a pH in the range of from about 12.5 to 13.5.

In general, the amount of alkaline protective polymer within an alkaline-providing composition employed in an analytical element of the invention depends upon the amount of base which is employed in the composition. In general, for each one part by weight of base present, approximately 2 to about 5 parts by weight of alkaline protective polymer have been found to provide useful results. Of course, depending upon the particular alkaline protective polymer under consideration, the particular basic compound to be admixed therewith, and the structure of the analytical element into which the alkaline-providing composition is to be incorporated, it is possible that one can obtain useful results within the scope of the invention using amounts of alkaline protective polymer outside the aforementioned range.

Reagent compositions which are incorporated in the analytical elements of the invention can include any of a wide variety of active materials. These materials interact chemically or physically and provide for a detectable change within the element upon treatment of the element with analyte-containing aqueous liquid. It is not unusual for a particular reagent composition to include several different active materials which may undergo a multiplicity of individual physical or chemical interactions upon treatment of an analytical element containing this reagent composition with analyte-containing aqueous liquid. Because a given reagent composition can contain more than one active material, the individual active materials can be distributed in more than one location, e.g., in more than one zone, of an analytical element of the invention. Accordingly, in a multi-zone analytical element of the invention, each of the active materials of the reagent composition used therein need not be incorporated solely in the reagent zone of the element. For example, one or more of the active materials of a given reagent composition employed in an integral multilayer analytical element may be incorporated in the spreading layer, or one of the other optional layers of the element such as a radiation-blocking layer, registration layer, filter layer, or other interlayers of the element as described hereinafter. Of course, in any case, at least one and often each of the active materials contained in a given reagent composition is incorporated in the reagent zone of the analytical element. In addition, it will be appreciated that a given analytical element in accord with the invention may contain more than one reagent zone.

The specific composition of the reagent compositions employed in the elements of the present invention can vary considerably depending upon the particular analyte applied to the element and on the particular detection means used to analyze for the presence of a detectable change within the element. In general, it will be appreciated that the present invention is compatible and particularly useful with those reagent compositions which contain one or more active materials that are interactive in a highly alkaline environment. It will further be appreciated that for any given analyte, there may be several different kinds of interactive compositions which could be employed.

In general, it will be appreciated that the reagent compositions employed in the present invention contain one or more active materials which either are directly detectable in their own right or are capable of interacting with one another, the analyte, or an analyte decomposition or reaction product to form a material which is detectable. In this way, there is provided the necessary active materials in a reagent composition to produce a detectable change within an analytical element of the invention upon application thereto of an aqueous sample containing the desired analyte.

As will be appreciated, a wide variety of different materials can be employed as the active materials of reagent compositions useful in the present invention. These active materials include colorimetrically detectable dyes and pigments, fluorometrically detectable dyes and pigments, radioactive tags, tagged antigen-antibody complexes, enzymes, and precursors and reaction products of these materials. For further detail, with respect to these materials reference may be made to U.S. Pat. 3,992,158 and U.S. Ser. No. 759,527 noted above.

As mentioned earlier herein, the present invention is particularly useful with a biuret reagent composition. Biuret reagent compositions interact with protein contained in aqueous fluids such as serum or plasma in the presence of a highly alkaline environment, e.g. at pH levels of 12.0 and preferably at 12.5 or higher. As a result of this interaction, the biuret reagent undergoes a readily detectable color change becoming violet in the presence of protein. As is well-known, the components of conventional biuret reagent compositions comprise a cupric salt, particularly a water-soluble cupric salt, and if desired, a chelating agent to reduce and prevent precipitation of insoluble copper hydroxide. Various surfactants may also be optionally incorporated in a biuret reagent composition. A variety of different cupric salts and chelating agents have been employed in prior art biuret reagent compositions. A partial list of representative such cupric salts includes cupric perchlorate, cupric sulfate, cupric acetate, cupric butyrate, cupric bromate, cupric chlorate, cupric bromide, cupric chloride, cupric fluoride, cupric dichromate, cupric formate, cupric iodate, cupric lactate, cupric orthophosphate, cupric laurate, cupric salicylate, cupric nitrate, cupric tartrate and cupric oxalate. An especially preferred cupric salt is cupric sulfate.

A partial list of representative chelating agents (or stabilizing agents as they are sometimes called) includes tartrates, citrates, ethylenediamine and the like. Additional examples and further details concerning cupric salts, chelating agents, and various surfactants which can be used in biuret reagent compositions can be found by reference to the publications noted in the "Related Art" section hereof.

The alkaline-providing compositions employed in the present invention are especially useful with the above-described biuret reagent compositions because of their requirement for a highly alkaline environment. When the alkaline-providing compositions employed in the invention are used together with a biuret reagent composition in an analytical element of the invention, they can be located in a zone of the element separate from, but in fluid contact with, the zone in which the biuret reagent composition is incorporated. Preferably, however, the alkaline-providing composition is located in the same zone as the biuret reagent composition, and the basic compound of the alkaline-providing composition becomes an integral part of the biuret reagent composition.

In accord with an especially preferred embodiment of the invention there is provided an improved biuret reagent composition. In accord with this embodiment, the entire biuret reagent composition is substantially free from sodium ion and comprises a water soluble cupric salt, a copper chelating agent precursor, and an amount of base sufficient to provide a pH in excess of about 12.0 under conditions of use of the biuret composition. The copper chelating agent precursor represents a material, such as tartaric acid, which under the highly alkaline conditions of use of the biuret reagent composition is converted into a copper chelating agent, e.g. a tartrate salt in the case of tartaric acid. In this embodiment of the invention, one especially preferred biuret reagent composition is a substantially sodium-free admixture of cupric sulfate, tartaric acid, and lithium hydroxide.

The amounts of the various components employed in the improved biuret reagent compositions of the invention can vary, depending in part on the protein analyte concentration range over which a specific biuret reagent composition is to be effective. In general, there should be from about 0.5 g. to about 10 g. of water soluble cupric salt for each gram of protein to be analyzed. The amount of copper chelating agent precursor depends in general on the amount of cupric salt present in the composition, there typically being present from about 0.5 to about 2 moles of chelating agent for each mole of cupric salt.

The above-described improved biuret reagent composition is particularly suitable for use in a "dry chemistry" analytical element of the present invention; however, it may also be employed as a biuret reagent composition in a "wet chemistry" assay of protein contained in an aqueous liquid sample. Techniques and procedures for carrying out such "wet chemistry" assays employing a biuret reagent are well-known and hence extensive discussion of these procedures are unnecessary herein. If desired additional information concerning these "wet chemistry" assays may be obtained by reference to the appropriate publications noted herein in the "Related Art" section.

When the improved biuret reagent compositions of the invention are incorporated into a dry chemistry analytical element as described herein, they are advantageously incorporated into a reagent zone thereof together with an alkaline-protective polymer as described above. Other non-interfering addenda such as surfactants, additional polymers as binders, and the like may also be incorporated into these reagent zones together with the improved biuret reagent composition and alkaline-protective polymer.

As indicated hereinabove the stable alkaline-providing compositions, as well as the improved biuret reagent compositions, described herein can be employed in a broad spectrum of "dry chemistry" analytical elements including a variety of structural configurations and materials. For example, these compositions can be incorporated in analytical element structures including relatively uncomplicated "dip and read" test strips; multi-zone analytical elements having a support bearing a spreading zone abutting an associated reagent zone as described in FIG. 2 of the above-referenced U.S. Ser. No. 759,529; and integral multilayer analytical elements having a radiation-transmissive support bearing two or more superposed contiguous layers including reagent layers, spreading layers, registration layers, radiation-blocking layers, filter layers, and subbing layers, as described in U.S. Pat. Nos. 3,992,158; 4,042,335; and Ser. No. 759,527. For purposes of convenience and for illustrating the best mode of the invention at the present time, the invention will hereinafter be described as embodied in the aforementioned integral multilayer analytical elements. However, it will be appreciated that a variety of other element structures may embody the invention broadly described herein.

An integral multilayer analytical element of the invention typically includes a spreading layer and a reagent layer, both of which are preferably radiation-transmissive. Such elements can have the layers on a support, preferably a radiation-transmissive support; however, if the layers demonstrate appropriate durability and integrity, a support is not needed.

In one preferred embodiment, an integral analytical element of this invention comprises a radiation-transmissive support having thereon, (1) a reagent layer that is permeable to water and dissolved active materials of a reagent composition, e.g., a biuret reagent composition, contained therein, and (2) a spreading layer that is permeable to water. The reagent layer is interposed between the support and the spreading layer. The spreading layer is preferably of substantially uniform permeability to dissolved components of an applied aqueous liquid sample. In those embodiments wherein the element contains a biuret reagent composition in the reagent layer, the spreading layer is also preferably of substantially uniform permeability to the dissolved active materials of the biuret composition of the reagent layer, thereby allowing these dissolved materials to migrate into the spreading layer. In these embodiments the reagent layer is preferably substantially impermeable to proteins, e.g., albumin and other proteins having a molecular weight in the region of 60,000 (dalton units) or higher. As a result, the dissolved materials of the biuret reagent composition interact with the protein held in the spreading layer of the element.

In accordance with a further aspect of the present invention, there is provided an integral analytical element with a support having thereon a reagent layer and a spreading layer, all as described above with respect to the foregoing preferred embodiment. Additionally, however, there is included in elements according to this preferred embodiment a non-fibrous spreading layer, desirably isotropically porous. In one aspect of this embodiment, all layers are preferably non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading or with detection of the analytical result by radiometric means.

Preferred spreading layers can be prepared using a variety of components as more fully described in the aforementioned U.S. Pat. No. 3,992,158. In one aspect, particulate material can be used to form such layers, the isotropic porosity of these layers being created by interconnected spaces between the particles. Various types of particulate matter, all desirably chemically inert to sample components under analysis, are useful including pigments, e.g., titanium dioxide; particles of diatomaceous earth; glass beads; plastic beads; and microcrystalline colloidal materials derived from natural or synthetic polymers, e.g. microcrystalline cellulose.

As an alternative or in addition to such particulate materials, the spreading layer can be prepared using isotropically porous polymer compositions. It is possible to prepare such polymer compositions using techniques useful in forming blushed polymers, for example, as described in U.S. Pat. No. 3,555,129 and in the aforementioned U.S. Pat. No. 3,992,158. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575. Many different polymers can be used, singly or in combination, for preparing isotropically porous blushed polymer spreading layers for use in this invention, typical examples being polycarbonates, polyamides, polyurethanes and cellulose esters such as cellulose acetate.

The thickness of the spreading layer and the pore size thereof is variable and will depend in part on the intended analyte size, the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements. Spreading layer pore sizes of from about 1 to about 30 microns have been found useful.

Reagent layers in the elements of this invention are desirably uniformly permeable to water and dissolved substances contained therein but substantially impermeable and nonporous to higher molecular protein materials. As used herein the term permeability includes permeability arising from porosity, ability to swell, or any other characteristic. Reagent layers can include a matrix, for example, a film-forming polymer in which the reagent composition is distributed, i.e., dissolved or dispersed. However, as is often the case in the present invention where the reagent layer incorporates the stable, alkaline-providing composition which itself contains the above-described alkaline-protective polymer, a separate matrix material for the reagent layer may be unnecessary, providing the alkaline protective polymer is present in sufficient amount.

The choice of a matrix material is, of course, variable and dependent on the components of the reagent composition and any other components distributed therein. In any case, the matrix material should be "non-interfering" with respect to the reagent composition, i.e., the matrix material should be incapable of itself binding or interacting with the active materials of the reagent composition. Preferred matrix materials for reagent layers associated with spreading layers are non-fibrous and can include non-interfering hydrophilic materials including gelatins, hydrophilic cellulose derivatives, polysaccharides such as dextran, gum arabic, and the like, and also synthetic substances such as water-soluble polyvinyl compounds like poly(vinyl alcohol), etc. Non-interfering materials such as cellulose esters and the like can also be useful. To enhance permeability of the reagent layer, if not porous, a matrix material can be used that is swellable in the solvent or dispersion medium of liquid under analysis. Also, it may be necessary to select a material that is compatible with the application of an adjacent layer, such as by coating means, during manufacture of the element. As an example, where the formation of discrete, contiguous layers is desired and the intended analysis will be of aqueous liquids, it may be appropriate to select an essentially water soluble matrix for the reagent layer and essentially organic solvent soluble or organic solvent dispersible ingredients for an adjacent layer, such as a spreading layer. In such manner, mutual solvent action is minimized and a clearly delineated layer structure can be formed. In many cases, to prevent diffusion of high molecular weight proteins into the reagent layer, it may be desirable to have the reagent layer of lower permeability than is the spreading layer itself. This can readily be accomplished by reducing the effective pore size of the reagent layer. Relative permeability or porosity can be determined by well-known techniques.

Within the reagent layer is distributed one or more components of the reagent composition to be employed in the particular analytical element being prepared. The distribution of reagent component(s) can be obtained by dissolving or dispersing it in a matrix material, if used. Although uniform distributions are often preferred, they may not be necessary. In addition, as noted above, the alkaline-providing compositions employed in the elements of the present invention may be incorporated in the reagent layer thereof.

The thickness of any reagent layer and its degree of permeability are widely variable and depend on actual usage. Dry thicknesses of from about 10 microns to about 100 microns have been convenient, although more widely varying thicknesses may be preferable in certain circumstances. Fibrous reagent layers can be formed by impregnation of a fibrous matrix, in accordance with well-known techniques.

In preparing integral analytical elements of this invention, the layers can be preformed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by various well-known coating techniques as described in further detail in the aforementioned U.S. Pat. No. 3,992,158. Any interlayer adhesion problems can be overcome without harmful effect by means of surface treatments including extremely thin application of subbing materials such as are used in photographic films.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 300 nm and about 700 nm.

In the layers of the element, it can be advantageous to incorporate one or more surfactants such as ionic or nonionic surfactants. They can, for example, enhance coatability of layer formulations and enhance the extent and rate of spreading in spreading layers that are not easily wetted by liquid samples in the absence of an aid such as a surfactant.

Analytical elements of the present invention can be adapted for use not only in the field of clinical chemistry, but in chemical research and in chemical process control laboratories. They are well suited for use in clinical testing of body fluids, such as blood, serum and urine, because in this work a large number of repetitive tests are frequently conducted and test results are often needed a very short time after the sample is taken.

As mentioned previously, elements of this invention can include a radiation-blocking layer. Radiation-blocking layers serve to inhibit passage of electromagnetic radiation, such as at the wavelength or wavelengths used for detection. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers can be used also as radiation-blocking layers.

In addition to the use of an optional radiation-blocking layer in an integral analytical element of the invention, other optional interlayers may also be incorporated, if desired. For instance, registration layers to receive detectable materials, e.g., dyes formed or released in the element as described in U.S. Pat. Nos. 3,992,158 and 4,042,335; filter layers; and interlayers containing various active materials of a reagent composition to interact with and thereby effectively remove any potential interferents for the particular analysis being carried out can be employed.

As can be appreciated, a variety of different elements can be prepared in accordance with the present invention. Elements can be configured in a variety of forms, including elongated tapes of any desired width, sheets or smaller chips.

The preferred integral elements are placed in use by applying to the element a sample of liquid under analysis. Typically, an element will be formed such that an applied sample will contact a spreading layer prior to the reagent layer and will first contact such spreading layer at its surface furthest removed from such reagent layer. Because analytical accuracy of the present elements is not substantially diminished by variations in the volume of applied samples, sample application by hand or machine is acceptable. For reasons of convenience in detecting an analytical result, however, reasonable consistency in sample volume may be desirable.

In a typical analytical procedure using the present integral elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, the element is exposed to any conditioning, such as heating, humidification or the like, that may be desirable to quicken or otherwise facilitate obtaining any test result.

After the analytical result is obtained as a detectable change, it is measured, usually by passing the element through a zone in which suitable apparatus for reflection or transmission spectrophotometry is provided. Such apparatus would serve to direct a beam of energy, such as light, through the support and the reagent layer. The light would then be reflected, such as from an opacifying agent in the spreading or a radiation-blocking layer in the element, back to a detecting means or would pass through the element to a detector, in the case of transmission detection. In a preferred mode, the analytical result is detected in a region of the element totally within the region in which such result is produced. Generally, electromagnetic radiation in the range of from about 400 to about 700 nm has been found useful for such measurements, although any radiation to which the element is permeable and which is capable of quantifying the detectable change produced in the element can be used. Various calibration techniques can be used to provide a control for the analysis. As one example, a sample of analyte standard solution can be applied adjacent to the area where the drop of sample is placed in order to permit the use of differential measurements in the analysis.

The following examples are presented to further illustrate the invention. The first example discloses a synthesis of one of the preferred alkaline protective polymers employed in the present invention. The second example discloses the results obtained by employing the off-line test described earlier herein for evaluating the suitability of a series of polymers for use as an alkaline protective polymer in accord with the invention.

EXAMPLE 1

Synthesis of Poly(acrylamide-co-N-vinyl-2-pyrrolidone) having a 50:50 monomer weight ratio To 2700 ml distilled water was added 900 g denatured alcohol, 200 g acrylamide and 200 g vinyl pyrrolidone. The solution was sparged with nitrogen gas and brought to 60° C. in a round bottomed flask equipped with N₂ inlet, reflux condenser and stirrer. A solution consisting of six grams of the polymerization initiator 2,2'-azobis(2-methylpropionitrile) dissolved in 60 ml acetone was then added to the above-noted monomer solution. After 16 hours at 60° C., the resultant clear viscous solution had a bulk viscosity of 125 cps at 10.8% solids. The inherent viscosity measured in 1 N NaCl on isolated polymer was 0.94.

EXAMPLE 2

Off-Line Test of Polymers For Alkaline Protective Capability

In this Example the alkaline protective capability of 6 separate polymers was evaluated using the Off-Line Test described earlier herein. The six polymers tested in this Example were as follows:

Polymer No. 1 — poly(acrylamide-co-N-vinyl-2-pyrrolidone) as described in Example 1
Polymer No. 2 — poly(acrylamide-co-2-hydroxyethyl acrylate) 50:50 monomer weight ratio)
Polymer No. 3 — poly(2-hydroxyethyl acrylate)
Polymer No. 4 — poly(acrylamide)
Polymer No. 5 — poly(vinyl pyrrolidone) purchased as K-90 polymer from GAF Corp.
Polymer No. 6 — sea plague agarose The results of the Off-Line Test evaluation of these six polymers is illustrated graphically in FIG. 1. As shown in FIG. 1, Polymer No. 1 exhibited excellent alkaline protective capability over the entire 8 day test period, whereas Polymer Nos. 2 and 3 exhibited very poor alkaline protective capability. As shown in FIG. 1 the compositions containing Polymer Nos. 2 and 3 exhibited low base content immediately after coating. It is believed that the polymers of these compositions exhibited poor alkaline protective capacity because of the hydrolysis sites present in the ester groups of these polymers which can be hydrolyzed by base. As can be seen in FIG. 1, Polymer Nos. 4 and 5 also exhibited acceptable alkaline protective capability during the eight day test period. As indicated by the data points in FIG. 1, additionl tests of Polymer Nos. 1-5 were continued beyond the eight day test period.

In a separate test, a coating composition identical to that used to evaluate Polymer Nos. 1-5 noted above was prepared, except that a sixth polymer, sea plague agarose purchased from Marine Colloids, Inc., was employed. This material was tested in a manner very similar to the above-described Off-Line Test and was also found to exhibit very good alkaline protective capability. The broken line portion of the graph in FIG. 1 for Polymer No. 6 merely indicates that the alkaline protective capability of this polymer was not tested during the period of time covered by the broken line. Testing of Polymer No. 6 was also carried beyond the eight day Off-Line Test period.

EXAMPLE 3

Multilayer Analytical Element for Determination of Total Protein

In this example a multilayer analytical element incorporating both an alkaline protective polymer composition and an improved biuret reagent composition in accord with the present invention was prepared. In this example, a multilayer element structure was prepared as follows:

A poly(ethylene terephthalate) film support was coated with a reagent layer comprising agarose as an alkaline protective polymer (16.0 g/m²), $CuSO_4 \cdot 5H_2O$ (10.8 g/m²), LiOH (5.4 g/m²), tartaric acid (8.0 g/m²), and a spreading layer comprising microcrystalline cellulose particles, i.e., Avicel® purchased from FMC Corp. (64.5 g/m²), and poly(vinylpyrrolidone) (1.6 g/m²).

A series of elements having the structure described above were evaluated colorimetrically by monitoring the change in reflection density, $D_R$, of a beam of light transmitted through a 540 nm. interference filter and then through the film support of the elements and then reflected by the spreading layer back through the film support. The changes in $D_R$ readings were monitored for each element at 37° C. as an aqueous solution containing a known amount of protein (albumin was used as the protein) ranging from 2–12% w./v. (weight/unit volume) was spotted onto the element. The $D_R$ of each element as it responded to the particular albumin-containing sample spotted therein was observed from 0–7 minutes. The development of color in the spreading layer of the element resulting from the biuret reaction ocurring in the element was found to be very rapid; the reaction of 2–7% (w./v.) protein-containing sample was over in less than 1 minute. Above 7% (w./v.) protein, reaction times were extended to about 7 minutes. The 7 minutes $D_R$ value for each sample tested is listed in Table I.

Table I

| % protein in sample | $D_R$ (540 mn) |
|---|---|
| 2 | 0.10 |
| 4 | 0.20 |
| 6 | 0.37 |
| 7 | 0.42 |
| 8 | 0.58 |
| 10 | 0.64 |
| 12 | 0.68 |

EXAMPLE 4

Stability of Sodium Free Alkaline-Providing Compositions

To demonstrate certain of the improvements and advantages of the present invention, two multilayer analytical elements were prepared in this example. Each was prepared in a manner identical to that described in Example 3 above, except that one of the elements, the Control, was prepared with sodium hydroxide as base, rather than lithium hydroxide. A series of each of the elements was then evaluated as in Example 3 using aqueous solutions containing protein levels ranging from 2–10% (w/v). Each element was evaluated immediately after its manufacture and then re-evaluated after being stored under ambient conditions, 21° C. and 50% R.H., for a period of 18 days. The $D_R$ values were recorded for each evaluation and are illustrated below in Table II. As can be seen from the results in Table II, the analytical element of the present invention, which contained lithium hyroxide and was free from sodium ion, produced $D_R$ values which were quite stable over the entire 18 day storage period. In contrast, the Control element containing sodium hydroxide showed a dramatic loss in sensitivity after 18 days storage.

Table II

| Element | Protein Content (%) | $D_R$ (as measured immediately after element manufacture) | $D_R$ (as measured after 18 days storage) |
|---|---|---|---|
| Element with LiOH | 2.5 | 0.19 | 0.16 |
| " | 5.0 | 0.32 | 0.27 |
| " | 7.5 | 0.58 | 0.55 |
| " | 10.0 | 0.85 | 0.74 |
| Control Element with NaOH | 2.5 | 0.13 | 0.13 |
| " | 5.0 | 0.32 | 0.18 |
| " | 7.5 | 0.51 | 0.22 |
| " | 10.0 | 0.70 | 0.26 |

EXAMPLE 5

Multilayer Analytical Element for Determination of Total Protein

In this example a multilayer analytical element for determination of total protein was prepared identically to that described in Example 3, except that the alkaline protective polymer agarose used in Example 3 was replaced with poly(acrylamide-co-N-vinyl-2-pyrrolidone) prepared as described in Example 1. The element was evaluated for its responsiveness to serum solutions containing protein levels ranging from 4 to 12% (w/v.) using the same procedure described in Example 3 above. Good element response was obtained. Due to improved linearity of element response, the overall performance of this element was considered to be even better than that provided by the element of Example 3. In addition, better adhesion and improved coatability of the reagent layer was obtained for this element containing the above-noted copolymer in comparison to that obtained for the reagent layer of the element of Example 3 which contained agarose.

The invention has been described in detail with particular reference to certain preferred embodiments thereof, but it will be understood that variations and modifications can be effected within the spirit and scope of the invention.

We claim:

1. In an analytical element for the detection of a predetermined analyte in an aqueous liquid, said element having
   (1) a zone to distribute said analyte, and
   (2) associated with said zone, a reagent composition that provides a detectable change within said element upon interaction of said element with analyte-containing liquid;
the improvement wherein said element contains a stable, alkaline-providing composition substantially free from sodium ion and comprising, in admixture,
   (a) an amount of base sufficient to provide a pH in excess of about 12.0 in said element under conditions of use thereof, and
   (b) an alkaline protective polymer.

2. An analytical element as defined in claim 1 wherein said base is selected from the group consisting of lithium hydroxide, calcium hydroxide, and mixtures thereof.

3. An analytical element as defined in claim 1 wherein said base is lithium hydroxide.

4. An analytical element as defined in claim 1 wherein said alkaline protective polymer is selected from the group consisting of agarose, poly(acrylamide), and polymers having a repeating unit derived from vinyl pyrrolidone.

5. An analytical element as defined in claim 1 wherein said alkaline protective polymer is selected from the group consisting of poly(vinyl pyrrolidone) and copolymers of acrylamide and vinyl pyrrolidone.

6. An analytical element as defined in claim 1 wherein said alkaline protective polymer is a copolymer prepared from a monomer blend comprising from about 20 to about 80 weight percent vinyl pyrrolidone and from about 80 to about 20 weight percent acrylamide.

7. An analytical element as defined in claim 1 wherein said base is lithium hydroxide and said alkaline protective polymer is a copolymer of acrylamide and vinyl pyrrolidone.

8. An analytical element as defined in claim 1 wherein said alkaline protective polymer is agarose.

9. An analytical element as defined in claim 1 wherein said alkaline-providing composition contains from about 2 to about 5 parts by weight of said polymer for each part by weight of said base.

10. A multi-zone analytical element for the detection of a predetermined analyte in an aqueous liquid, said element comprising a spreading zone and a reagent zone in fluid contact under conditions of use, said reagent zone comprising a reagent composition that provides a detectable change within said element upon interaction of said element with analyte-containing liquid, said reagent composition comprising at least one active material interactive at a pH in excess of about 12.0, said element containing a stable, alkaline-providing composition substantially free from sodium ion and comprising, in admixture,
   (a) an amount of base sufficient to provide a pH in excess of about 12.0 in said reagent zone under conditions of use of said element, and
   (b) an alkaline protective polymer.

11. A multi-zone analytical element as defined in claim 10 wherein said alkaline-providing composition is in said reagent zone.

12. A multi-zone analytical element as defined in claim 10 wherein said reagent composition comprises a biuret reagent composition and said element provides for the detection of protein in an aqueous liquid.

13. A multi-zone analytical element as defined in claim 10 wherein said alkaline-providing composition contains lithium hydroxide.

14. A multi-zone analytical element as defined in claim 10 wherein said alkaline protective polymer is selected from the group consisting of agarose and polymers having a repeating unit derived from vinyl pyrrolidone.

15. A multi-zone analytical element as defined in claim 10 wherein said alkaline protective polymer is a copolymer of acrylamide and vinyl pyrrolidone.

16. A multi-zone analytical element for the detection of protein in an aqueous liquid, said element comprising a radiation-transmissive support bearing,
   (1) a radiation-transmissive spreading zone to distribute said aqueous liquid, and
   (2) a reagent zone in fluid contact with said spreading zone under conditions of use of said element, said reagent zone containing a biuret reagent composition substantially free from sodium ion and comprising, in admixture, a water soluble cupric salt, a copper chelating agent precursor, and a stable, alkaline-providing composition, said alkaline-providing composition comprising
      (a) an amount of base sufficient to effect the interaction of said cupric salt with said protein thereby providing a radiometrically detectable change under conditions of use of said element, and (b) an alkaline protective polymer.

17. A multi-zone analytical element as defined in claim 16 wherein said copper chelating agent precursor is tartaric acid and said alkaline-providing composition comprises, in admixture, lithium hydroxide and a polymer selected from the group consisting of agarose and polymers having a repeating unit derived from vinyl pyrrolidone.

18. A multi-zone analytical element as defined in claim 16 wherein said copper chelating agent precursor is tartaric acid and said alkaline-providing composition comprises, in admixture, lithium hyroxide and a polymer containing a repeating unit derived from vinyl pyrrolidone.

19. A multi-zone analytical element as defined in claim 16 wherein said copper chelating agent precursor is tartaric acid and said alkaline-providing composition comprises, in admixture, lithium hydroxide and a copolymer of acrylamide and vinyl pyrrolidone.

20. An integral multilayer analytical element for the detection of a predetermined analyte in an aqueous liquid, said element having at least two superposed layers comprising a spreading layer and a reagent layer, said two layers being in fluid contact under conditions of use of said element, said reagent layer comprising a reagent composition that provides a detectable change within said element upon interaction of said element with analyte-containing liquid, said reagent composition comprising at least one active material interactive at a pH in excess of about 12.0, said element containing a stable, alkaline-providing composition substantially free from sodium ion and comprising, in admixture, (a) an amount of base sufficient to provide a pH in excess of about 12.0 in said reagent layer under conditions of use of said element, and (b) an alkaline protective polymer.

21. An integral multilayer analytical element as defined in claim 20 wherein said alkaline-providing composition is in said reagent layer.

22. An integral multilayer analytical element as defined in claim 20 wherein said reagent composition comprises a biuret reagent composition and said element provides for the detection of protein in an aqueous liquid.

23. An integral multilayer analytical element as defined in claim 20 wherein said alkaline-providing composition contains lithium hydroxide.

24. An integral multilayer analytical element as defined in claim 20 wherein said alkaline-providing composition contains, in admixture, lithium hydroxide and a copolymer of acrylamide and vinyl pyrrolidone.

25. An integral multilayer analytical element as defined in claim 20 wherein said spreading layer comprises a non-fibrous composition.

26. An integral multilayer analytical element as defined in claim 20 wherein said alkaline protective polymer is a copolymer prepared from a monomer blend comprising from about 20 to about 80 weight percent vinyl pyrrolidone and from about 80 to about 20 weight percent acrylamide.

27. An integral multilayer analytical element as defined in claim 20 wherein said alkaline-providing composition contains from about 2 to about 5 parts by weight of said polymer for each part by weight of said base.

28. An integral multilayer analytical element for the detection of protein in an aqueous liquid, said element comprising a radiation-transmissive support bearing at least two superposed layers comprising a spreading layer and a reagent layer, said two layers being in fluid contact under conditions of use of said element, said reagent layer being interposed between said spreading layer and said support and said reagent layer comprising a biuret reagent composition to produce a radiometrically detectable change upon interaction of said protein with said biuret reagent composition, said element containing a stable, alkaline-providing composition substantially free from sodium ion and comprising, in admixture, (a) an amount of base sufficient to provide a pH in excess of about 12.0 in said reagent layer under conditions of use of said element, and (b) an alkaline protective polymer.

29. An integral multilayer analytical element for the assay of total protein in serum, said element comprising a radiation-transmissive support bearing at least two superposed layers comprising (1) a spreading layer permeable to said aqueous liquid, and (2) a reagent layer in fluid contact with said spreading layer under conditions of use of said element, said reagent layer being interposed between said support and said spreading layer, and said reagent layer containing a biuret composition substantially free from sodium ion and comprising, in admixture, a water soluble cupric salt, tartaric acid, and a stable, alkaline-providing composition comprising (a) an amount of base sufficient to effect the interaction of said cupric salt with said protein, thereby producing a radiometrically detectable change under conditions of use of said element, and (b) an alkaline protective polymer.

30. An integral multilayer analytical element as defined in claim 29 wherein said alkaline-providing composition comprises, in admixture, lithium hydroxide and a polymer selected from the group consisting of agarose and polymers having a repeating unit derived from vinyl pyrrolidone.

31. An integral multilayer analytical element as defined in claim 29 wherein said alkaline-providing composition comprises, in admixture, lithium hydroxide and a polymer containing a repeating unit derived from vinyl pyrrolidone.

32. An integral multilayer analytical element as defined in claim 29 wherein said alkaline-providing composition comprises, in admixture, lithium hydroxide and a copolymer of acrylamide and vinyl pyrrolidone.

33. An integral multilayer analytical element as defined in claim 29 wherein said spreading layer comprises a non-fibrous composition.

34. An integral multilayer analytical element as defined in claim 29 wherein said cupric salt is copper sulfate.

35. An integral multilayer analytical element as defined in claim 29 wherein said alkaline protective polymer is a copolymer prepared from a monomer blend comprising from about 20 to about 80 weight percent vinyl pyrrolidone and from about 80 to about 20 weight percent acrylamide.

36. A method for the detection of protein in an aqueous liquid sample which comprises (1) applying said sample to a multi-zone analytical element having a radiation-transmissive support bearing
 (a) a radiation-transmissive spreading zone to distribute said aqueous liquid, and
 (b) a reagent zone in fluid contact with said spreading zone under conditions of use of said element, said reagent zone containing a biuret reagent composition substantially free from sodium ion and comprising, in admixture, a water soluble cupric salt, a copper chelating agent precursor, and a stable, alkaline-providing composition, said alkaline-providing composition comprising
  (i) an amount of base sufficient to effect interaction of said protein with said cupric salt thereby producing a radiometrically detectable change in said element, and
  (ii) an alkaline protective polymer, and
(2) radiometrically detecting, after a predetermined time, said detectable change.

37. A method as defined in claim 36 wherein said alkaline-providing composition comprises lithium hydroxide and a copolymer of acrylamide and vinyl pyrrolidone.

38. A method for the detection of protein in an aqueous liquid sample which comprises
(1) applying said sample to an integral multilayer analytical element, having a radiation-transmissive support bearing at least two superposed layers comprising
 (a) a spreading layer permeable to said aqueous liquid, and
 (b) a reagent layer in fluid contact with said spreading layer under conditions of use of said element, said reagent layer being interposed between said support and said spreading layer, and said reagent layer containing a biuret composition substantially free from sodium ion and comprising, in admixture, a cupric salt, tartaric acid, and a stable, alkaline-providing composition comprising
  (i) an amount of base sufficient to effect the interaction of said cupric salt thereby producing a radiometrically detectable change in said element, and
  (ii) an alkaline protective polymer, and
(2) radiometrically detecting, after a predetermined time, said detectable change.

39. A method as defined in claim 38 wherein said alkaline-providing composition comprises lithium hydroxide and a copolymer of acrylamide and vinyl pyrrolidone.

40. A biuret reagent composition substantially free from sodium ion comprising, in admixture, a water soluble cupric salt, a copper chelating agent precursor, and an amount of a base sufficient to provide a pH to said composition under conditions of use in excess of about 12.0.

41. A biuret reagent composition as defined in claim 40 wherein said chelating agent precursor is tartaric acid and said base is lithium hydroxide, calcium hydroxide, or a mixture thereof.

42. A biuret reagent composition substantially free from sodium ion comprising, in admixture, copper sulfate, tartaric acid, and lithium hydroxide.

43. A method for the detection of a predetermined analyte in an aqueous liquid sample, said method comprising
 (a) contacting together said sample and an analytical element that provides a detectable change upon interaction of said element with said sample, said element containing a stable alkaline-providing composition substantially free from sodium ion and comprising, in admixture,
  (i) an amount of base sufficient to provide a pH in said element during said contacting step (a) in excess of about 12.0, and
  (ii) an alkaline protective polymer; and
 (b) detecting, after a predetermined time, said detectable change.

44. In a method for the detection of a predetermined analyte in an aqueous liquid sample, said method comprising
 (a) contacting together said sample and a reagent composition that provides a detectable change upon interaction with analyte-containing liquid, and
 (b) detecting, after a predetermined time, said detectable change,
the improvement which comprises prior to said detecting step (b), contacting together said sample and a stable alkaline-providing composition substantially free from sodium ion and comprising, in admixture,
  (i) an amount of base sufficient to provide a pH in excess of about 12.0 upon interaction of said sample and said reagent composition in said contacting step (a), and
  (ii) an alkaline protective polymer.

45. A method for analysis of protein in an aqueous liquid sample which comprises
 (a) treating said sample with a biuret reagent to produce a radiometrically detectable color change upon interaction of said protein with said biuret reagent, said biuret reagent composed of a composition substantially free from sodium ion and comprising, in admixture, a water soluble cupric salt, a copper chelating agent precursor, and an amount of base sufficient to provide a pH during said treatment with said sample in excess of about 12.0; and
 (b) detecting said color change.

46. A method for analysis of protein as defined in claim 45 wherein said biuret reagent comprises copper sulfate, tartaric acid, and lithium hydroxide.

* * * * *